(12) United States Patent
Viala et al.

(10) Patent No.: US 12,351,769 B2
(45) Date of Patent: Jul. 8, 2025

(54) PLANT FOR PRODUCING METHANE

(71) Applicant: ARKOLIA ENERGIES, Mudaison (FR)

(72) Inventors: Audrey Viala, Mudaison (FR); Mickael Scudeller, Mudaison (FR); Laurent Bonhomme, Mudaison (FR); Stephane Hattou, Mudaison (FR)

(*) Notice: Subject to any disclaimer, the term of this patent is extended or adjusted under 35 U.S.C. 154(b) by 647 days.

(21) Appl. No.: 17/756,191

(22) PCT Filed: Nov. 19, 2019

(86) PCT No.: PCT/FR2019/052746
§ 371 (c)(1),
(2) Date: May 19, 2022

(87) PCT Pub. No.: WO2021/099695
PCT Pub. Date: May 27, 2021

(65) Prior Publication Data
US 2022/0411706 A1   Dec. 29, 2022

(51) Int. Cl.
*C10L 3/08*   (2006.01)

(52) U.S. Cl.
CPC ............ *C10L 3/08* (2013.01); *C10L 2290/10* (2013.01); *C10L 2290/36* (2013.01); *C10L 2290/38* (2013.01)

(58) Field of Classification Search
CPC .... C10L 3/08; C10L 2290/10; C10L 2290/36; C10L 2290/38; C10L 2290/146; C10L 2290/46; C10L 2290/562; Y02P 20/133
See application file for complete search history.

(56) References Cited

FOREIGN PATENT DOCUMENTS

| | | |
|---|---|---|
| DE | 1110147 B | 7/1961 |
| DE | 102009018126 A1 | 10/2010 |
| DE | 102011013922 A1 | 9/2012 |
| FR | 3019410 A1 | 10/2015 |
| FR | 3081471 A1 | 11/2019 |
| WO | 2012110257 A1 | 8/2012 |
| WO | 2014207703 A1 | 12/2014 |

OTHER PUBLICATIONS

ISR; European Patent Office; Aug. 11, 2020.
Elham Ahmadi Moghaddam et al: "Exploring the Potential for Biomethane Production by Willow Pyrolysis Using Life Cycle Assessment Methodology"; Feb. 22, 2019.

*Primary Examiner* — Jafar F Parsa
(74) *Attorney, Agent, or Firm* — Patshegen IP; Moshe Pinchas

(57) ABSTRACT

The methane production plant consists of several key components, including an electric energy source, an electrolyser that supplies hydrogen gas, an atmospheric carbon dioxide capture device that provides carbon dioxide and water, and a methanation reactor that produces methane using the hydrogen, water, and carbon dioxide. Additionally, the plant features solar collectors and a heat transfer system that supplies heat from the solar collectors to the carbon dioxide capture device.

14 Claims, 4 Drawing Sheets

PLANT FOR PRODUCING METHANE

TECHNICAL FIELD

The present invention relates to a plant and a method for producing methane. It is particularly applicable to the production of methane based on solar energy.

STATE OF THE ART

Power-to-Gas is one solution to the growth in renewable energy production plants. This is because renewable energies are variable and consequently there can be electricity over-production peaks at times when consumption is low in France. By creating a storage solution, Power-to-Gas is highly relevant to this configuration, as the transformation of electricity into gas makes it possible to make use of a loss of electricity as an energy carrier via hydrogen or methane.

This Power-to-Gas model is built as follows: the electricity generated by renewable sources is transformed into hydrogen via an electrolyser. The process may end with this production and have several uses: injection into the grids; mobility; compression and storage. However, hydrogen (in $H_2$ gas form) is not an easily storable and transferable energy carrier.

DESCRIPTION OF THE INVENTION

The present invention aims to remedy all or part of these drawbacks.

To this end, the present invention envisages a plant for producing methane, which comprises:
- an electric energy source;
- a water electrolyser supplied with electrical energy from the electric energy source, suitable for producing hydrogen in gas form;
- an atmospheric carbon dioxide capture device suitable for supplying carbon dioxide and water;
- a methanation reactor, fitted with an inlet for hydrogen from the electrolyser, and with an inlet for water and carbon dioxide from the atmospheric carbon dioxide capture device, and suitable for producing methane; and
- solar collectors and a means for transferring heat from the solar collectors to the carbon dioxide capture device.

Thanks to these arrangements, the plant's water requirement is reduced, since at least part of the methanation reactor's water requirement is provided by the atmospheric carbon dioxide capture device.

In some embodiments, the plant comprises a means for collecting run-off water from the solar collectors, the electrolyser comprising an inlet for run-off water collected on the solar collectors.

In some embodiments, the electrical energy source comprises photovoltaic panels, the plant comprising a means for collecting run-off water from the photovoltaic panels, the electrolyser comprising an inlet for run-off water collected on the photovoltaic panels.

In some embodiments, the plant comprises a dehydration unit for the methane output by the methanation reactor, the methanation reactor comprising an inlet for water from the dehydration unit.

In some embodiments, the plant comprises a dehydration unit for the methane output by the methanation reactor, suitable for supplying water to the electrolyser inlet.

Each of these embodiments makes water savings possible.

In some embodiments, the electrolyser is suitable for electrolysing water output by the methanation reactor.

In some embodiments, the electrolyser is suitable for electrolysing water output from the atmospheric carbon dioxide capture device.

In some embodiments, the plant comprises a heat transfer means suitable for transferring heat from the electrolyser to the carbon dioxide capture device.

In some embodiments, the plant comprises a heat transfer means suitable for transferring heat from the methanation reactor to the carbon dioxide capture device.

In some embodiments, the electrical energy source comprises photovoltaic panels fitted with a cooling system, the plant comprising a heat transfer means suitable for transferring heat from the photovoltaic panels to the carbon dioxide capture device.

In some embodiments, the plant comprises a compressor for compressing the methane produced by the methanation reactor and injecting it into a gas transportation or distribution grid, and a heat transfer means suitable for transferring heat from the compressor to the carbon dioxide capture device.

In some embodiments, the electrolyser is suitable for supplying a portion of the heat required for the carbon dioxide capture device to operate.

In some embodiments, the methanation reactor is suitable for supplying a portion of the heat required for the carbon dioxide capture device to operate.

In some embodiments, the electrical energy source comprises photovoltaic panels fitted with a cooling system suitable for supplying a portion of the heat required for the carbon dioxide capture device to operate.

In some embodiments, the plant comprises a compressor for compressing the methane produced by the methanation reactor and injecting it into a gas transportation or distribution grid, a portion of the heat required for operating the carbon dioxide capture device being supplied by the compressor.

Each of these embodiments saves heat and avoids having to consume electrical energy produced by the photovoltaic panels to supply heat to the carbon dioxide capture device.

In some embodiments, the methanation reactor is a methanogenesis reactor.

In some embodiments, the methanation reactor is a catalytic methanation reactor.

In some embodiments, the methanation reactor is a thermochemical methanogenesis reactor.

BRIEF DESCRIPTION OF THE FIGURES

Other advantages, aims and characteristics of the present invention will become apparent from the description that will follow, made, as an example that is in no way limiting, with reference to the drawings included in an appendix, wherein.

DESCRIPTION OF EMBODIMENTS OF THE INVENTION

Figure 1:
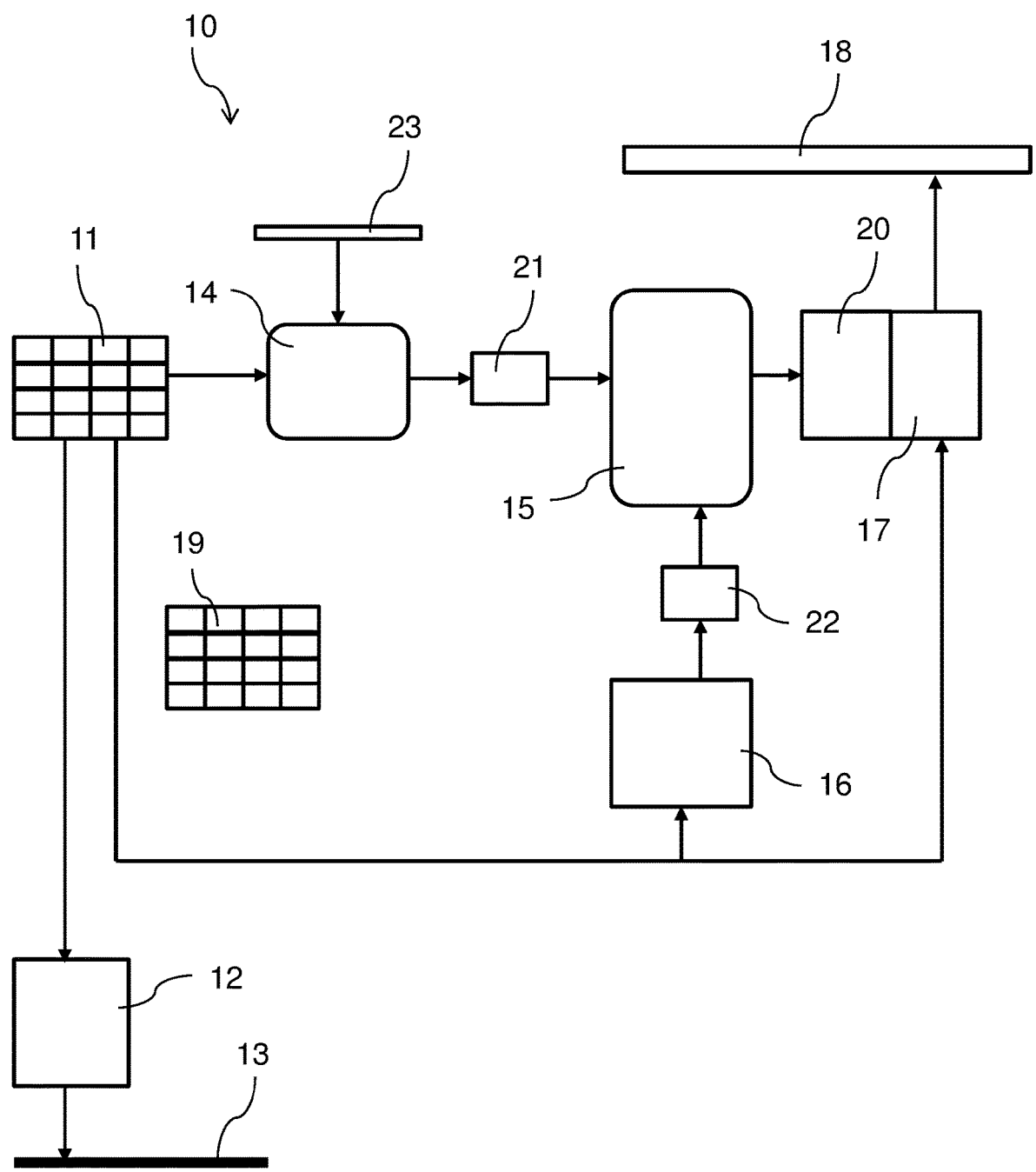
FIG. 1 represents, in a block diagram, a particular embodiment of the mixed-energy production plant that is the subject of the invention.

It is noted that the figures are not to scale. FIG. 1 shows a mixed-energy production plant 10, which energy is in the form of electricity injected into an electricity grid 13 and methane injected into a gas transportation and/or distribution 18. The plant 10 comprises an electric energy source, for example, photovoltaic (or "solar") panels producing direct current electricity, and a transformer 12 that produces alternating current electricity at the voltage and frequency of the electricity grid 13.

In some variants, the photovoltaic panels 11 are replaced with another electricity source whose production may be surplus to the consumption over the electricity grid, or relative to the transport capacity of the portion of the electricity grid connected to the electricity source, for example wind turbines or even a nuclear power plant.

The plant 10 also comprises an electrolysis unit (or "electrolyser") 14 producing hydrogen ($H_2$), which is stored in a tank 21. In addition, the tank 21 is connected by means of a pipe fitted with a valve to one inlet of a methanation reactor 15. A source 16 of carbon dioxide ($CO_2$) produces carbon dioxide, which is stored in a tank 22. In addition, the tank 22 is connected by means of a pipe fitted with a valve to the methanation reactor 15. A dehydration unit 20 with its output connected to a compressor 17 supplies pressurised methane to a gas grid 18. Depending on the embodiments, the methanation reactor 15 is a methanogenesis reactor, a catalytic methanation reactor or a thermochemical methanogenesis reactor.

For a methanogenesis reactor 15, bacteria consume the hydrogen ($H_2$) and the carbon dioxide ($CO_2$) to produce methane ($CH_4$) per the equation:

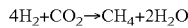

$$4H_2 + CO_2 \rightarrow CH_4 + 2H_2O$$

As this equation shows, this production of methane is accompanied by heat being released and water being produced.

Methanogenesis, or biomethanation, is a biological process that occurs at a temperature of between 40 and 80° C. and a pressure lower than 10 bars. Methanogenesis enables the conversion of hydrogen ($H_2$) and carbon dioxide ($CO_2$) into methane ($CH_4$) by means of an anaerobic microbial consortium. There are two types of methanogenesis:

In-situ: the hydrogen is injected into a biogas plant, where the most favourable hydrogenotrophic activity is located; and Ex-situ: the hydrogen is injected into a dedicated reactor, which operates under optimised conditions (temperature, residence time, biomass type and nutrient intake).

The energy efficiency in kWh GCV of the methanogenesis reactor is 78% for methane ($CH_4$) production and 20% for heat. Concerning the conversions of $H_2$ and $CO_2$: at least 98% of the $H_2$ is converted, and the efficiency of the carbon atom conversion of the carbon dioxide $CO_2$ into $CH_4$ is at least 98%.

One benefit of methanogenesis is that it can operate intermittently: once the stability conditions are met, the bacteria are not overly sensitive to variations in the quantities of gas in the $H_2$ and $CO_2$ feedstock: this load can become null or return to the nominal flow-rate with no effect on the conversion of $CO_2$ and $H_2$ into $CH_4$. For this reason, methanogenesis is suitable for ground-mounted photovoltaics.

Furthermore, with regard to carbon dioxide ($CO_2$), methanation is not overly sensitive to imperfections and can accept low contents of hydrogen sulphide ($H_2S$), ammonia ($NH_3$), and hydrogen ($O_2$).

In some less preferred embodiments, methanogenesis is replaced by catalytic methanation with the same chemical equation. This chemical methanation occurs at a temperature of between 250 and 350° C. and a pressure of between 10 and 20 bars, and is sensitive to sulphide. In some embodiments, the methanogenesis utilises a thermomechanical process.

The carbon dioxide ($CO_2$) source 16 is preferably a carbon dioxide capture device utilising direct air capture. Such a source is described, for example, in document US 2017 326 494, incorporated by reference, and in the documents cited therein, which are also incorporated by reference.

The separation of gas by adsorption makes it possible to target a specific component of a gas stream. A significant application consists of capturing carbon dioxide ($CO_2$) from gas streams, for example from atmospheric air.

Several atmospheric $CO_2$ capture methods have been developed based of various technological approaches. For example, U.S. Pat. No. 8,163,066 describes structures and techniques for capturing and regenerating carbon dioxide. Document US 2009/0120288 describes a method for removing carbon dioxide from the air. Document US 2012/0174778 describes a method for capturing and regenerating carbon dioxide utilising a vertical lift. Document WO2010022339 describes a method and plant for capturing carbon dioxide. These four documents are incorporated herein by reference.

A particular approach is based on a cyclic adsorption/desorption step on solid and chemically functionalised materials. For example, document WO2010 091831 discloses a structure based on solid adsorbent materials functionalised by an amine, jointly with a carbon adsorption/desorption method using this material for extracting carbon dioxide from ambient air. This document is incorporated herein by reference.

In this case, the adsorption process occurs in ambient conditions where the air is diffused through the adsorbent material and a portion of the $CO_2$ contained in the air is chemically bonded to the surface functionalised by the amine of the material. During the subsequent desorption, the material is heated to approximately 50-110° C. and the partial pressure of carbon dioxide surrounding the material is reduced by applying vacuum or exposing the material to a flow of purge gas. In this way, the carbon dioxide previously captured is removed from the adsorbent material and obtained in concentrated form.

Document WO2012 168346A1, incorporated herein by reference, discloses a material based on cellulose functionalised by an amine that can be used for the method described above.

Preferably, the material is an amine-modified material, preferably based on weak base ion-exchange resin, specifically polystyrene matrix material modified by amine groups, especially primary amine groups or based on cellulose, nanofibrillated cellulose, preferably, in each case, with a mean particle diameter in the range 60 to 1200 μm, for adsorbing carbon dioxide.

In a typical cyclic adsorption and desorption method, adsorption can occur in ambient conditions, for example within a temperature range of −30 to 40° C. and an absolute pressure of 0.7 to 1.3 bar.

After the carbon dioxide or the carbon dioxide and water vapor has been adsorbed, the absorbent material can be regenerated by heating it to, for example, 50 to 120° C., and by reducing the partial $CO_2$ pressure around the adsorbent material by reducing the absolute pressure to, for example, 1 to 250 mbar, i.e., applying vacuum and/or exposing the material to a purge gas flow. If the desorption is achieved by heating the material and applying vacuum, the entire cyclic process is called "temperature-vacuum swing" (TVS) process. If the desorption is achieved by heating the material and exposing it to a purge gas stream, the overall cyclic process is called "temperature concentration sweep" (TCS) process.

In some embodiments, the individual layers of material are formed on rigid chassis structures, each comprising a rectangular frame with an edge length of 0.5 m×0.6 m and a height of 1 cm, made of stainless steel extruded sections.

Manufacturing and assembling the overall structure comprises the following steps:
1. The chassis structures are manufactured by welding stainless steel extruded sections or by injection moulding of plastic or aluminium material;
2. Inside the frames, an aluminium grid and a rubber tube containing a heat-transfer fluid are inserted to provide proper heat-transfer;
3. A layer of non-woven fabric is bonded to both sides (top and bottom) of the frame structure using a two-component adhesive.
4. A material based on cellulose fibres modified by an amine is produced according to an enhanced version of the procedure described in document WO2012 168346:
   a. Cellulose nanofibers are isolated from the refined suspension of fibrous beech wood pulp (see "1. Isolation of cellulose nanofibers" in WO2012 168346, incorporated herein by reference);
   b. A solution of hydrolysed 3-aminopropyl methyldiethoxysilane is added to a nanofiber suspension with a 3.2% dry mass content;
   c. The solution is homogenised and stirred for two hours;
   d. Batches of the solution are frozen in copper in liquid nitrogen;
   e. The frozen mixture is lyophilised for 48 hours;
   f. The dried matter is processed at 120° C. in an argon-atmosphere oven; and
   g. The material is compressed and grated to obtain a granular material with a mean particle size of approximately 400 µm;
5. The material is injected into the frame structure through an opening, which is then closed;
6. A layer of absorbent material is obtained. The thickness of this layer varies between 1 and 1.5 cm;
7. Overall, 26 frames are stacked on one another, while distant parts form the input and output channels;
8. The stack is assembled inside a rectangular vacuum chamber with internal dimensions of 0.55 m×0.55 m×0.65 m, with an inlet and an output opening for the air stream;
9. A pneumatically-actuated butterfly valve is connected to each of the openings to seal off and open the chamber from/to the environment;
10. The input opening is connected to a fan to produce the air stream during adsorption. In addition, the chamber is connected to a vacuum pump to reduce the pressure during desorption and to a thermostat to heat and cool the stack during the steps of the individual cycle.

With the proposed structure, it is possible to extract a substantial portion of the $CO_2$ contained in an atmospheric air stream by using an amine-modified material with a pressure drop of less than 100 Pa, with a structure that can be manufactured with little force.

In the case shown in FIG. 1, where the carbon dioxide source 16 is an atmospheric air carbon dioxide carbon capture device, solar collectors 19 heat a heat-transfer fluid (pressurised water, oil, or molten salt).

In some embodiments, the $CO_2$ comes from biogas coming from a biogas plant processing wastewater treatment plant sludge, for example.

The dehydration unit 20 makes it possible for the methane injected into the gas grid 18 to meet the specifications for gas supplied to consumers connected to this grid 18. Note that this dehydration unit produces water. The compressor 17 compresses the pressurised methane. Because of the laws of thermodynamics, the compressor 17 also produces heat. Furthermore, the specifications of the gas grid 18 may require that the compressed gas be cooled, meaning that an additional amount of heat must be collected.

Figure 2:
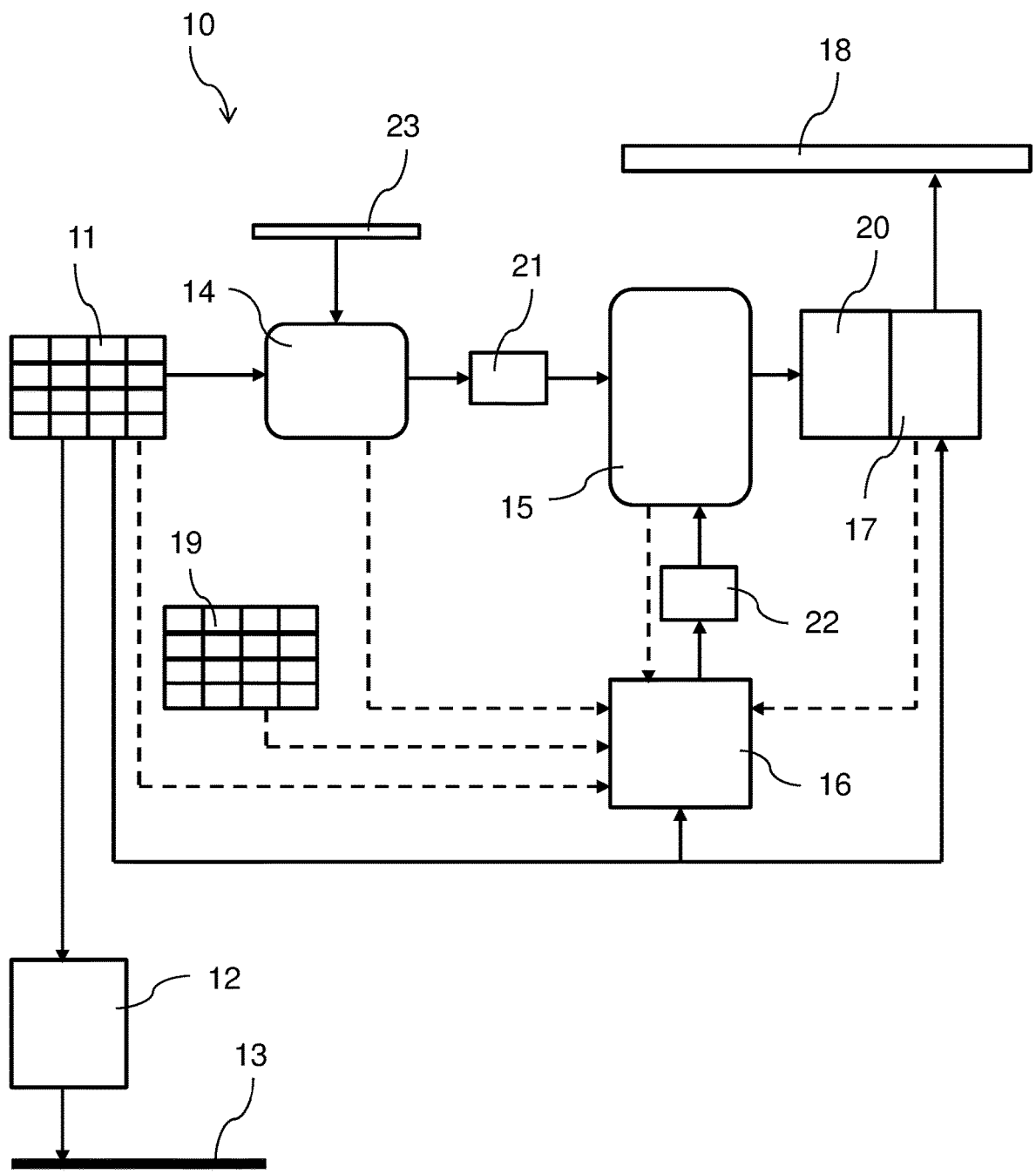
FIG. 2 represents, in a block diagram, the heat transfers between various different parts of the plant illustrated in FIG. 1.

In FIG. 2, heat transfers are shown by thin dashed lines. These heat-transfers are made by heat-transfer means (not shown) comprising heat exchangers and a means for moving heat-transfer fluid in pipes fitted with valves (not shown) between the heat exchangers (not shown). As illustrated in FIG. 2, in the case of a $CO_2$ source 16 that requires heat, for example an atmospheric carbon dioxide capture device, this heat is at least partly produced and supplied by:
   solar collectors 19 heating a heat-transfer fluid (for example pressurised water, oil, or molten salt);
   the electrolysis unit 14 (preferably 20 to 40% of the heat requirement of the source 16);
   the methanation reactor 15 (preferably 20 to 40% of the heat requirement of the source 16);
   a system (not shown) for cooling the photovoltaic panels 11 and/or the compressor 17.

As an option, a geothermal energy unit (not shown) supplies heat to the source 16.

Figure 3:
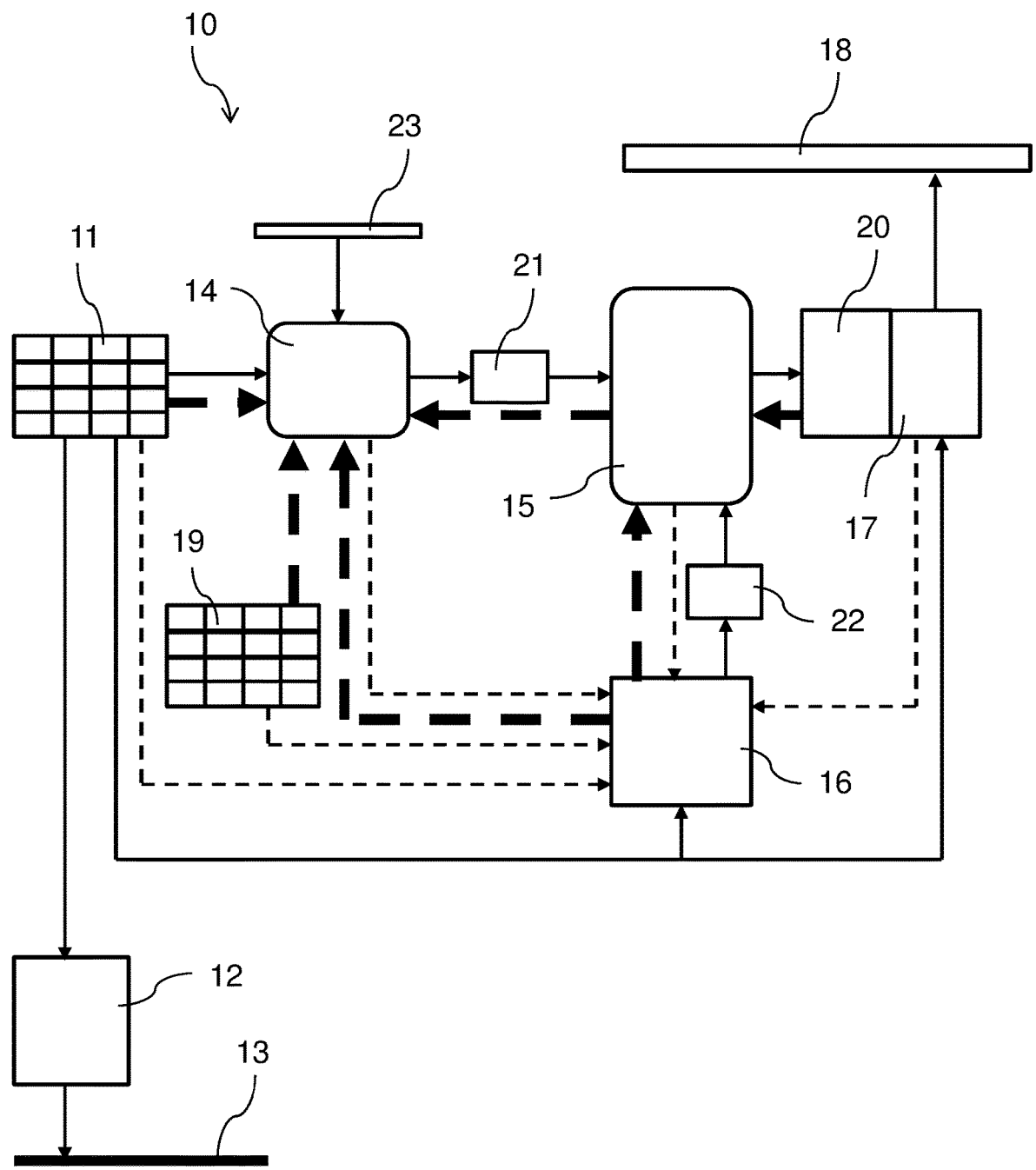
FIG. 3 represents, in a block diagram, in addition to the heat transfers, the water transfers between various parts of the plant illustrated in FIGS. 1 and 2.

In FIG. 3, water transfers are shown by thick dashed lines. These water transfers correspond to pipes fitted with valves (not shown). As illustrated in FIG. 3, water produced by the carbon dioxide ($CO_2$) source 16 is transferred to the methanation reactor 15 and used in the methanation reactor 15, for example to dilute the nutriment required by the anaerobic microbial consortium. Preferably, the water produced by the carbon dioxide ($CO_2$) source 16 covers the entire water requirement of the methanation reactor 15 when in continuous operation. In other words, the methanation reactor comprises no other water inlet open during its continuous operation than the one receiving water produced by the carbon dioxide source 16.

Water produced by the dehydration unit 20 is transported for input into the methanation reactor 15 and/or the electrolysis unit 14. Water produced by the methanation reactor 15 is transported for input into the electrolysis unit 14. Preferably, between 40% and 80% of the water used by the electrolysis unit 14 can be supplied by the methanation reactor 15. Note that, nevertheless, in this case it is preferable to purify the water. In addition, the plant comprises a means (not shown) for collecting run-off water from the photovoltaic panels 11 and/or the solar collectors 19. This collected run-off water is transported for input to the electrolysis unit 14 to cover, for example, up to 40% of the water requirements of the electrolysis unit 14. Optionally, as illustrated in FIG. 3, a portion (for example 15 to 35%) of the water consumption of the electrolysis unit 14 is water produced by the carbon dioxide ($CO_2$) source 16.

In some variants (not shown), the entire electricity production coming from the photovoltaic panels 11 is used to produce methane, rather than just surplus electricity.

As can be seen from reading the description above, the methane production plant 10 comprises, in particular:
- an electric energy source 11;
- a water electrolyser 14 supplied with electrical energy from the electric energy source, suitable for producing hydrogen in gas form;
- an atmospheric carbon dioxide capture device 16 suitable for producing carbon dioxide and water;
- a methanation reactor 15 fitted with an inlet for hydrogen from the electrolyser, fitted with an inlet for water and carbon dioxide from the atmospheric carbon dioxide capture device, and suitable for producing methane; and
- solar collectors 19 and a means for transferring heat from the solar collectors to the carbon dioxide capture device.

The plant 10 has many benefits. Renewable energy power plants produce low-cost intermittent electricity. A surplus portion of the electricity produced can be used, via water electrolysis, to produce $H_2$, which can be stored, albeit in fairly costly conditions. $CO_2$ capture and storage is a forward-looking solution to reduce pollution from industry and towns, as well as to meet the commitment to cut $CO_2$ emissions by a factor of four by 2050. The plant combines the benefits of $CO_2$ capture and storage with those of water electrolysis by utilising methanation and synergies in terms of heat and water flow. In this way, both capturing $CO_2$ from the air and making use of $CO_2$ in energy are achieved, resulting in one more step in the fight against climate change as well as for energy independence. With water being produced by this methanation technology (for methanogenesis, substantially one metric ton of water per metric ton of carbon dioxide captured), the mixed-energy production plant's water requirement is reduced.

Figure 4:
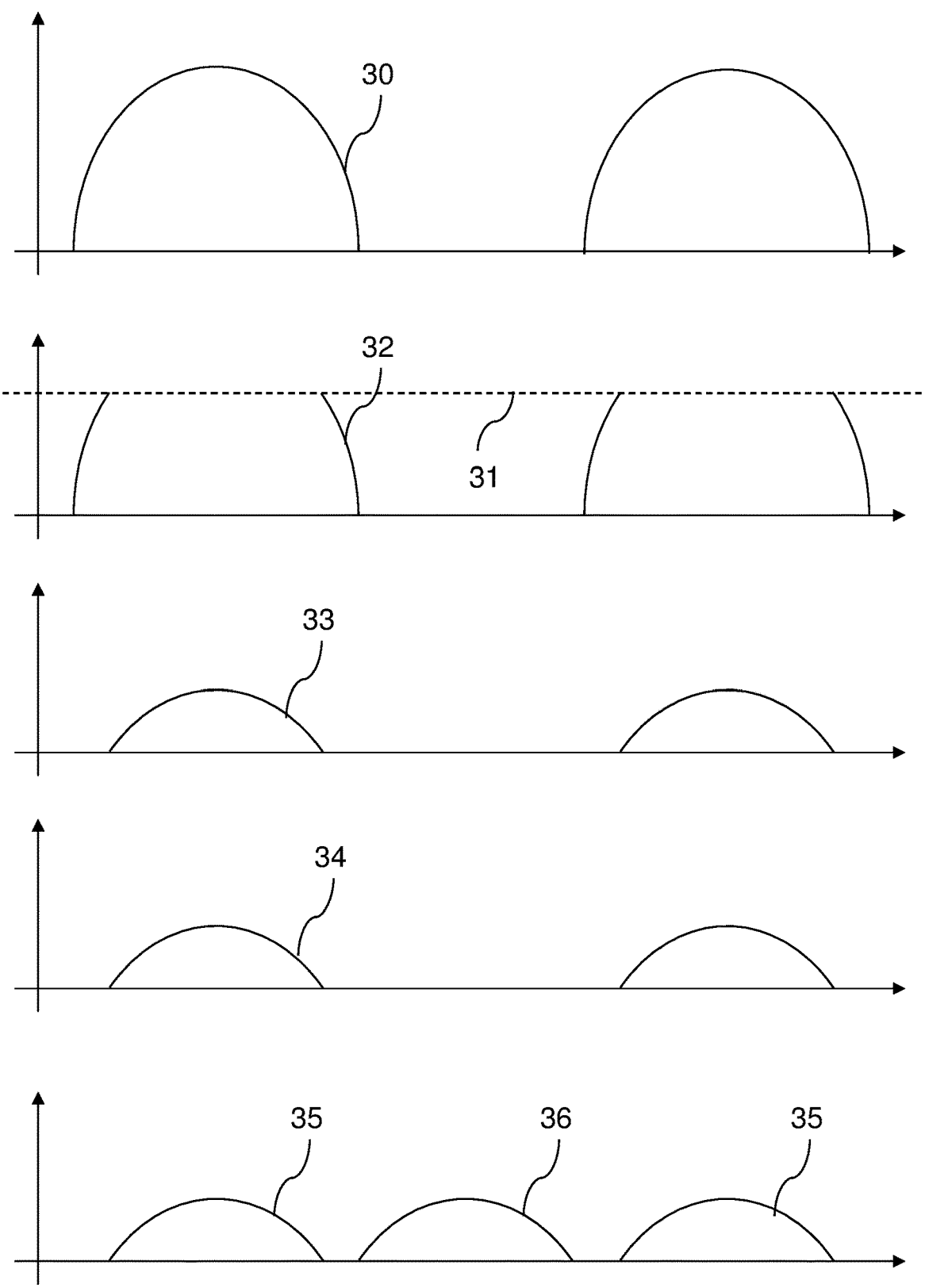
FIG. 4 represents, as curves, the operation of various systems of the plant illustrated in FIGS. 1 to 3.

FIG. 4 shows a curve 30 of electricity production over time during two successive days. This curve exhibits a lobe for each sunny day, the night-time production being null.

An electricity production limit value 31 can also be seen, beyond which electricity production is surplus, as the electricity grid 13 cannot absorb electricity produced above this limit value 31. This limit value 31 can be fixed over time, for example because of the sizing of the electrical cables connected to the plant 10, as surmised in FIG. 4. This limit value 31 can also be variable, depending on the energy consumption on the electricity grid 13. In this case, only the portion 32 of the electricity produced is supplied to the electricity grid 13. The portion 33 of the electricity produced supplies the systems of the plant 10, especially the electrolysis unit 14. Curve 34 represents the quantity of hydrogen produced. Curves 35 and 36 represent the operation of the carbon dioxide source 16.

Preferably, as illustrated in FIG. 4, during cold night hours, the source 16 adsorbs the atmospheric carbon dioxide ($CO_2$) in accordance with curve 36. In contrast, during the hottest daytime hours, the source 16 releases the adsorbed carbon dioxide and receives heat from the various components of the plant, as shown opposite FIG. 3. In a variant, the carbon dioxide ($CO_2$) capture and supply by the source 16 are performed alternatively in continuous manner throughout the period in which the photovoltaic panels 11 supply electricity.

In a variant (not shown), all the electricity produced by the photovoltaic panels is used to generate methane. In other words, the limit value 31 is null.

In a variant (not shown), depending on the seasons, more or less electricity or methane is produced by changing the limit value 31. For example, in winter—the time of year when gas consumption (for heating) is at its highest—the plant 10 is essentially used to produce methane, the limit value 31 then being low or null. Conversely, in summer—the time of year when gas consumption is at its lowest—the plant 10 is essentially used to produce electricity, the limit value 31 then being higher.

The invention claimed is:

1. A plant for producing methane, comprising:
an electric energy source;
a water electrolyser supplied with electrical energy from the electric energy source, suitable for producing hydrogen in gas form;
an atmospheric carbon dioxide capture device suitable for producing carbon dioxide and water;
a methanation reactor fitted with an inlet for hydrogen from the electrolyser, fitted with an inlet for water and carbon dioxide from the atmospheric carbon dioxide capture device, and suitable for producing methane; and
solar collectors and a means for heat transfer from the solar collectors to the carbon dioxide capture device.

2. The plant according to claim 1, which comprises a means of collecting run-off water from the solar collectors, the electrolyser comprising an inlet for run-off water collected on the solar collectors.

3. The plant according to claim 1, wherein the electrical energy source comprises photovoltaic panels, the plant comprising a means of collecting run-off water from the photovoltaic panels, the electrolyser comprising an inlet for run-off water collected on the photovoltaic panels.

4. The plant according to claim 1, which comprises a dehydration unit for the methane output by the methanation reactor, the methanation reactor comprising an inlet for water coming from the dehydration unit.

5. The plant according to claim 1, which comprises a dehydration unit for the methane output by the methanation reactor, suitable for supplying water to the electrolyser inlet.

6. The plant according to claim 1, wherein the electrolyser is suitable for electrolysing water output by the methanation reactor.

7. The plant according to claim 1, wherein the electrolyser is suitable for electrolysing water output from the atmospheric carbon dioxide capture device.

8. The plant according to claim 1, which comprises a heat transfer means suitable for transferring heat from the electrolyser to the carbon dioxide capture device.

9. The plant according to claim 1, which comprises a heat transfer means suitable for transferring heat from the methanation reactor to the carbon dioxide capture device.

10. The plant according to claim 1, wherein the electrical energy source comprises photovoltaic panels fitted with a cooling system, the plant comprising a heat transfer means suitable for transferring heat from the photovoltaic panels to the carbon dioxide capture device.

11. The plant according to claim 1, which comprises a compressor for compressing the methane produced by the methanation reactor and injecting it into a gas transportation or distribution grid; and a heat transfer means suitable for transferring heat from the compressor to the carbon dioxide capture device.

12. The plant according to claim 1, wherein the methanation reactor is a methanogenesis reactor.

13. The plant claim 1, wherein the methanation reactor is a catalytic methanation reactor.

14. The plant according to claim 1, wherein the methanation reactor is a thermochemical methanogenesis reactor.

* * * * *